(12) United States Patent
Schalkhammer

(10) Patent No.: US 8,673,237 B2
(45) Date of Patent: Mar. 18, 2014

(54) SENSOR HAVING A COLOR-CHANGEABLE SENSORY SURFACE

(76) Inventor: Thomas Schalkhammer, Kasten bei Böheimkirchen (AT)

( * ) Notice: Subject to any disclaimer, the term of this patent is extended or adjusted under 35 U.S.C. 154(b) by 65 days.

(21) Appl. No.: 13/389,505

(22) PCT Filed: Aug. 5, 2010

(86) PCT No.: PCT/AT2010/000283
§ 371 (c)(1),
(2), (4) Date: Apr. 3, 2012

(87) PCT Pub. No.: WO2011/017726
PCT Pub. Date: Feb. 17, 2011

(65) Prior Publication Data
US 2012/0183452 A1  Jul. 19, 2012

(30) Foreign Application Priority Data
Aug. 13, 2009  (AT) ................ A 1273/2009

(51) Int. Cl.
*G01N 21/75* (2006.01)
(52) U.S. Cl.
USPC ........ 422/421; 436/164; 436/165; 422/82.05; 422/430; 422/68.1
(58) Field of Classification Search
USPC .............. 422/421, 430, 82.05, 68.1
See application file for complete search history.

(56) References Cited

U.S. PATENT DOCUMENTS 5,611,998 A * 3/1997 Aussenegg et al. ........ 422/82.05

| | | |
|---|---|---|
| 5,639,671 A | 6/1997 | Bogart et al. |
| RE37,412 E | 10/2001 | Aussenegg et al. |
| 6,669,906 B1 | 12/2003 | Schalkhammer et al. |
| 2003/0174384 A1 | 9/2003 | Halas et al. |
| 2004/0062682 A1 | 4/2004 | Rakow et al. |

(Continued)

FOREIGN PATENT DOCUMENTS

| | | |
|---|---|---|
| EP | 0 677 738 | 10/1995 |
| EP | 1 790 977 | 5/2007 |

(Continued)

OTHER PUBLICATIONS

International Search Report issued Dec. 1, 2010 in International (PCT) Application No. PCT/AT2010/000283.

*Primary Examiner* — Sally Merkling
(74) *Attorney, Agent, or Firm* — Wenderoth, Lind & Ponack, L.L.P.

(57) ABSTRACT

The invention relates to a sensor having a color-changeable sensory surface, characterized in that at least one molecular layer of a positively charged polymer (4) is bonded to a further molecular layer of a negatively charged polymer (5) in alternation by means of ionic forces, wherein a solvent is stored in the charged polymer layers (4, 5), whereby the polymer layers swell at least 10%, and colored, preferably metal or semiconducting nanoparticles (6) are bonded to the last charged polymer molecular layer, and the total layer thickness of the inert intermediate layer (3) and all polymer layers (4, 5) is at least 40 nm but less than 500 nm so that the layer setup has an interference color that is visible to the human eye or measurable in the infrared and that can be changed by means of interaction with an analyte, the interference color being caused by optical interference between the material surface (2) and the layer of the nanoparticles (6).

28 Claims, 4 Drawing Sheets

(56) References Cited

U.S. PATENT DOCUMENTS

Figure 1:
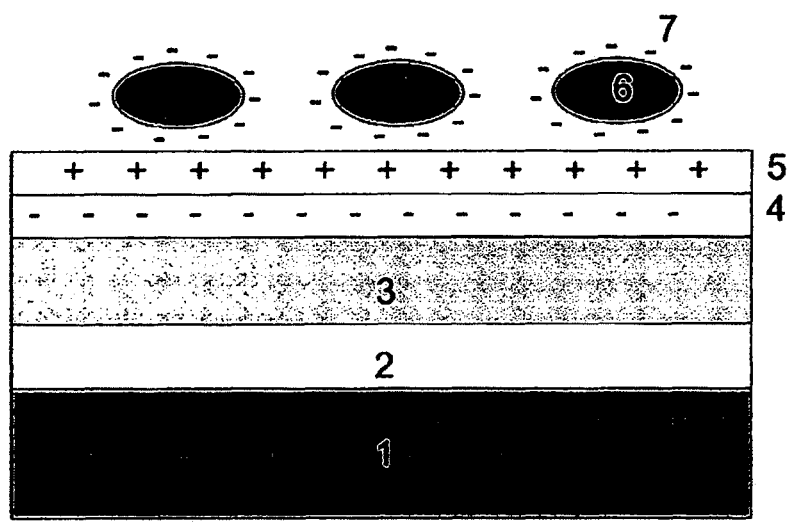

2004/0184948 A1 9/2004 Rakow et al.
2005/0019849 A1 1/2005 Desprez et al.
2008/0063575 A1 3/2008 Rakow et al.
2009/0035179 A1 2/2009 Rakow et al.

FOREIGN PATENT DOCUMENTS

| WO | 98/48275 | 10/1998 |
| WO | 2007/057905 | 5/2007 |
| WO | 2009/029964 | 3/2009 |

* cited by examiner

SENSOR HAVING A COLOR-CHANGEABLE SENSORY SURFACE

DESCRIPTION OF THE INVENTION

The invention relates to a sensor coated with multiple nano-layers having a color-changeable sensory surface, the color change being visible to the human eye and the nano-layers being applied directly onto the light wave-reflecting surface of a plate, a film, an injection molded or embossed part or onto sensor chips—as well as its novel method of manufacturing. The sensor has color-reactive properties primarily utilizable for intelligent packaging of consumer goods but also as sensory display. The sensor is especially suited for simple indication of humidity, indication of condensation water, indication that a temperature limit has been exceeded, indication of the temperature history (temp-time), for indication of complex chemical information (pH-value, ion concentration, . . . ), indication of food deterioration, indication of living germs as well as for indication of relevant biomedical data. The novel multi-polymer nanolayer basic structure and the novel manufacturing process is in all statements identical and is if need be modified in the desired way by additional exterior layers.

The integration of sensory tags and labels on films, labels or molded parts in and on paper, food packaging, in windows (sensor for thickness of insulating glazing), electronic devices of all kinds (ingress of moisture and water) allows avoiding damage and loss of quality and indicating the active status of the product. Also application in reactive-smart-intelligent design of products, which actively react to a chemical or physical stimulus with a color change, is reasonable and possible e.g. a sensor, which changes its color when touched.

The sensor with color-changeable sensory surface according to the invention is part of packaging, films and labels but can also be produced as molded part. The sensor has if need be an active color-changeable sensory surface reacting to proteins, DNA or other small ligands such as e.g. water, $CO_2$, organic vapors and solvents.

Physical Basis of the Color Effect

Based the physical effect of the resonance-enhanced absorption of nano-particles=interference of light (in the literature often called REA and protected by the inventor (Schalkhammer et al.) in further patents, for the first time in 1995) a novel structure is described in the configuration according to the invention, as well as its method of manufacturing, which serves as basis for a number of sensory films and labels.

Innovation According to the Invention
1) As required by the invention real nanotechnology using and assembling single molecule mono-layers is employed for the first time.
2) Surprisingly, it was found that resonance-enhanced colors may be created out of multiple molecularly thin layers with thicknesses of 1 molecule.
3) There are at least 2 (or several if need be) different polymers comprising at least one polymer with positive and one polymer with negative charge.
4) In contrast to all known structures the molecules lie on each other orderly, layer by layer and interact only with neighboring layers.
5) This completely new configuration allows manufacturing structures that are completely homogenous in thickness also on uneven surfaces for the first time—so far this hasn't been possible with any other known technology—with a precision of a few nanometers or optimally even with a deviation of less than one nanometer. To date only even, faultless films or flat pigment platelets could be used.
6) The process allows producing polymer layers even without vacuum processes (such as e.g. sputtering of evaporation coating) by multiple alternately dipping into at least 2 different, in most cases aqueous polymer solutions with binding times of less than 30 minutes per layer, optimally even less than 2 minutes.
7) As the layers (4, 5) exhibit a typical thickness of 3-4 nm (minimum: 1 nm-maximum: 20 nm) the construction of sensors exclusively out of molecule monolayers is often not reasonable and in most cases supplemented using an inert (not sensorily active) layer for adjusting the base color below the polymer monolayers.
8) Bonding of the layers consisting of weakly ionic or partially neutralized strongly ionic polymer monolayers allows applying them in a partially folded state, see FIG. 4. Only for this reason it is possible to allow a structural "swelling" of the layer and thereby a visible color change by intercalation of a solvent. Binding of the individual polymer monolayers in the (common) strongly charged state leads to rigid and structurally nearly inactive (flexible) multi-layers as all chains lie upon each other flat and unfolded and solvent cannot enter.
9) All known resonance colors with sensory properties make use of a polymer layer, which has been applied via precipitation, crosslinking, photoresist spin coating or printing e.g. via gravure printing. All these methods lead to qualitatively inferior products, because precipitation and crosslinking lead to inhomogeneous layer thickness, spin-coating is only possible on ultra-even small substrates and under completely dust-free conditions (semiconductor industry) and no printing technology allows sufficient quality within the required range of layer thickness of less than 300 nm and in most cases leave an imprint of the well pattern of the anilox roller. The novel process can be performed on films as well as on 3-dimensional molded or embossed parts and on small platelets in absolutely the same way. The process as described by the invention is the first process possessing these outstanding properties.

Explanations

The sensor according to the invention, primarily in most cases a film or a molded part is e.g. applicable for
1) the reversible indication and quantification of humidity (in the air) based on a multi-layered, ionically bound multi-polymer molecule film out of at least 2 but most often 4-12 molecular layers of hydratable polymer molecules, which are alternately positively and negatively charged and are applied onto an inert nanolayer (3);
2) a pigment with a bioreactively changeable nano-metrically-thin layer for the detection of bacteria and fungi to be used in food safety also based on a multi-layered ionically bound multi-nano-layer film out of at least 2 but in most cases 4-8 layers of hydratable polymer molecule monolayers, said film being changed in structure and thereby in thickness by interaction with metabolic products of the germs;
3) a novel freeze-thaw indicator pigment for cold chain monitoring also based on a multi-layered ionically bound multi-nano-layer film out of at least 2 but in most cases 4-8 layers of hydratable polymer molecule monolayers, the freezing/thawing leading to an irreversible collapse of the hydratable polymer molecule monolayers; being changed in structure and thereby in thickness by interaction with metabolic products of the germs.

The invention relates to the 6-20-layered configuration of the films and their process of manufacturing using multi-layered ionic polymer monolayers, which are applied molecule layer by molecule layer onto the reflecting surface and themselves are coated with nanoparticles, which also preferable occurs via ionic interactions to yield a resonance color effect. The nanoparticles are applied via physical/chemical methods from suspension in liquid or gas and in most cases carry a charge, which develops as a result of synthesis or is applied via a polymer on purpose. As a result of synthesis this can happen e.g. due to oxidation of the nanoparticles in air or via adsorption of other ionic synthesis components. High vacuum processes (sputtering, high vacuum evaporation) are usually not advantageous, as they are too expensive for the field of application and are not applicable for coating of powder and especially 3D-objects.

The resonance color configuration (=REA) provides the basis for a new type of sensory materials, which generate a signal that can be perceived with the eye and can be optically quantified easily. The key attribute of a resonance color system is a color change, which is induced by an external chemical or a physical stimulus such as atmospheric humidity, temperature, pH-value, microbial activity or molecular interaction.

By means of the resonance color technology, a technique, which has been studied by scientists at the universities of Wiener Neustadt (FHWN), Vienna and Graz as well as the TUDELFT (NL), and employed (bio-)analytically by Prof. Th. Schalkhammer for the first time and marketed by Attophotonics GmbH, a visual signal is generated by a change of the nanostructure.

The basics of the resonance color technology were described in: "Metal nano Clusters as transducers for bioaffinity interactions", invited review in Chemical Monthly 129, 1067-1092 (1998) by T. Schalkhammer; "Surface enhanced resonance of metal nano Clusters: A novel tool for Proteomics", Journal of Nanoparticle Research 3, 361-371 (2001) by C. Mayer, R. Palkovits, G. Bauer, T. Schalkhammer. First applications of the REA-nano-color technology were published in: "Food-allergen assays on chip based on metal nanocluster resonance", SPIE 4265, 134-141 (2001) by C. Mayer, R. Verheijen, Th. Schalkhammer and applications of REA-films in bioanalysis were described in: "Phage display antibody-based proteomic device using resonance-enhanced detection", J. Nanoscience and Nanotechnology 2V3/4,375-5 381 (2002) by N. Stich, A. Gandhum, V. Matyushin, J. Raats, Ch. Mayer, Y. Alguel, Th. Schalkhammer.

More specific details of the color effect were explained by the inventor e.g. in WO 2009/029964. Patent applications describing various resonance colors are known: OI: EP 1 790 977 AI, 02: EP O 677 738 AI, 03: US 2005/0019849 A1, 04: US 2004/0062682A 1, 05: U.S. Pat. No. 6,669,906 BI, 06: US 2003/0174384 AI, 07: U.S. RE37 412 E, 08: WO 2009/029964 A2 and 09: WO 2007/057905 A2.

In U.S. Pat. No. 5,611,998, Optochemical sensor and method for production, as well as in the derived reissue: U.S. RE37412, Optochemical sensor and method for production as sensor is described using a gel layer that is made swell or shrink upon action of a low-molecular analyte. An irreversible change is also described in this patent. In U.S. Pat. No. 6,669,906, Reinforced düster optical sensors, Schalkhammer et al. a configuration is known, in which the bond between reflective layer and nanoparticle is created by a specific in most cases biomolecule. Alteration of this bond leads to an optical signal. The configuration described in U.S. Pat. No. 5,611,998 consisting of mirror, swelling and nanoparticle layer is the general scientific basis or color effects—however, no product could be marketed, which uses this technology, as the configuration is based on spin coating technologies used in semiconductor technology or printing technologies, which do not allow industrial production (see above).

In the past years two paths were explored to create structures, which yield technically producible products. On the one hand the path of small base particles—most commonly aluminum flakes of 15-50 μm—was explored and novel reactor-based methods for coating were invented to produce printable sensory "nano-ink"—described e.g. in WO 2009/029964.

The present application describes a novel configuration, which allows creating a coating of high quality and homogeneous color in a completely novel way and thereby also on 3-dimensional objects (impossible hitherto) but also on films (hitherto laborious and of low quality). The process steps utilizable for the reactor technology and those utilizable for the film technology respectively excluded each other technologically until now. Efforts employing printing technology for printing of a distance layer between mirror and nanoparticle layer, e.g. using a water-swellable polymer, are described in patents—however, practical application shows massive problems as neither homogenous color quality nor sufficient color intensity can be yielded and in most cases the products exhibit an unavoidable color pattern due to the imprint of the employed gravure printing rollers.

The use of pigments, commonly aluminum pigments, coated with inert layers (without sensory properties) was described as effect pigment in a patent. This is a special technical variant of the REA-effect, of which the application for jewelry colors was already suggested upon its discovery.

The present application describes a "color sensor" of novel configuration and a novel technology of manufacturing, which allow generating high-quality coatings of homogenous color on 3D-objects or films, which, being used as intelligent labels, enable the user e.g. to optimize the shelf life of goods, to indicate the status of e.g. foodstuffs, maintain their nutritional value by correct storage, indicate the occurrence of microbial growth in packaged food.

Sensors for food products are often subdivided into 1. time/temperature indicators and integrators and 2. threshold indicators, which give a visual (optical) hint—both fields of application can be covered with the multi-nano-layer structures described in this invention. Particularly for the following products color-changeable sensory films can be created using the structure according to the invention: atmospheric humidity in food, electronics and pharmaceuticals, freeze-thaw indication, control of the state of microwave-heated products ("cooking state"), status of "microwave packaging systems", oxygen leaks in packaging, deterioration of fish, deterioration of meat, deterioration of poultry, rancid butter, milk—indicating deterioration, yoghurt, cream, sour cream, wet cheese—including bacterial infestation, cake, pudding, orange- or apple juice or other juices—deterioration, olive oil, quality control of baby food, cold chain, convenience food e.g. pizza, microwave ready, cooking sensor for microwave food, for film-wrapped vegetables, vegetables in glass jars, cans or conserved food packaging, cut flowers, pharmaceuticals in blister packaging—integrity and deterioration.

Market segments are already described in e.g. WO 2009/029964 for nano-printing inks and in most cases (with only few exceptions) analogously also hold good for the sensor film, sensor platelets and sensor tags according to this patent. The humidity-indicating, color-changeable sensory foils described in this patent are in general combined with desiccants and marketed along with food products, pharmaceuticals, medical equipment, electric/electronic components and clothes. The product according to the invention is an injection molded part or pierced pieces of films e.g. a logo integrated within packaging of e.g. meat and fish together with humidity regulators on fleeces.

The color-changeable sensory films described in this patent thereby protect consumers from unsafe food and provide unmistakable signals to the consumer. The color-changeable sensory color films according to this invention can be applied with standard laminating equipment. The films are applied online during the packaging process, are part of the packaging or are simply enclosed with the goods. The color-changeable sensory films and of the objects laminated with them must have a shelf-life of at least more than one year and the product must be stable in a wide temperature range. Fields of application of color-changeable sensory films is packaging of fresh food (meat, sausages, poultry, fish, cheese, vegetables). Primarily in the field of "convenience food" (in transparent bags or in trays), on milk products (microbial state, smell, taste), for registration of the state of added preservative agents, the status of light or UV-protection, the water content and the state of gas permeability (in case of dry food, especially chips, snacks, spices, coffee, pre-baked food, the product should be well protected from atmospheric humidity in order to stay crunchy, tender and tasty) the sensors could be used. Also in the field of hygiene products e.g. cosmetics (determined by high cleanness and safety), the microbial status as well as oxidation products of chemicals as well as in the medical field operation overalls, masks, "coverware" with a high level of sterility are reasonable fields of application. For the calibration of the color-changeable sensory films color-comparison panels and color charts are, as is common practice in engineering, added or packaged with the product for calibration.

Alternatively the sensory configuration according to the invention can be used to display text or symbols by applying the reactive colors in a way that upon reaction with an analyte (e.g. humidity change) parts of the sensor change their color—thereby e.g. a test becomes visible or a symbol vanishes. This variant of the sensor according to the invention does not require any additional color comparison panels or color charts and can at best even be used as display for the temporary of permanent display of text and other information.

The advantages according to the invention are:
- color-changeable sensory films, plates, platelets or 3D molded surfaces (not possible with any printing technology or photoresist spin coating!!!)
- environmentally friendly due to the use of novel, in most cases water-based manufacturing processes
- color and color change respectively are visible to the eye
- no bleaching at light & all colors with identical chemistry
- machine-readable
- allowing safety-technical encoding
- chemically sensitive color effects without soluble chemicals The configuration of resonant color systems is already described in previous patents of the applicant e.g. EP0677738; briefly: The configuration related to an optochemical sensor for measuring substance concentrations with a reactive sensory layer. Sensors of the type described at the beginning are essentially characterized in that they comprise a mirror layer, a reactive, particularly with solvents hydratable matrix and a layer out of a number of nanometrical particles out of electrically conducting material, especially metals or semiconductors. In such a sensor the property of sensor materials is made use of, to change the folding of polymer chains reversibly or irreversibly under the influence of the respective actual chemical environment. On this basis sensors that indicate the deterioration of an intermediate layer were also described (diploma thesis of Martin Dragosists, 2005, University of Vienna, supervising tutor Prof. Schalkhammer). The aim of the configuration according to the invention is not the development of sensors on the basis of the known configuration mirror—distance layer—nanoparticle layer—which is described easily but does not lead with any known and hitherto commercially utilizable technology to simple and cost-effectively marketable products, but it describes a novel, more complex molecule layer configuration with at least 6 but in most cases 12 layers, which due to novel manufacturing processes is attainable cost-efficiently and efficiently in terms of production technology. Hitherto is has been difficult to develop uniform and homogeneous distance layers out of polymers for resonance colors, i.e. which are suited for smart color-changeable sensory films, and exhibit no artifacts, holes, dirt particles, scratches but, in particular, an exact homogeneity in thickness (which becomes visible as color effect) as standard techniques like high vacuum coating, spin coating or printing techniques are not suited and cannot be used for the application of the color-relevant reactive interlayer or do not yield products that are homogeneous in color respectively.

Color-changeable sensory films allow the display of a signal, which is visible without instruments with the bare eye and, by that, is ideally suited for being applied on packaging, films or even directly on products.

There was considerable interest in the application of polymers, which exhibit a fundamental structural change upon small changes of environmental parameters, particularly of the solvation behavior. Well known stimuli, which lead to a change of the solvation behavior of polymer chains, are solvents, especially water, humidity, pH-value and ionic strength. The simplest color-changeable sensory films result from the use of water-reactive polymers with partially folded chains. It is known that by sequential adsorption of positively and negatively charges polymers a building up layers on surfaces is possible. These layers are highly rigid and are used particularly because of their stability—they consist of unfolded chains and have a thickness of approximately 2 nm per layer. They only weakly show solvation and swelling behavior. These known layers are thus not applicable as sensory layers as the number of required layers for a defined resonance color (e.g. 100 nm for the color green) often is 20-50 due to the low layer thickness. According to the invention folded chains could also be bound to the surface now and thus a structurally reactive material could be created. According to the invention at least partially folded chains (with a layer thickness per layer of more than 3 nanometers of considerably more) are used now, favorably all layers are in folded form and are applied as solvent by chemical/ionic binding onto an inert base layer applied by sol-gel-technology. The sol/gel-layer (3) can also be replaced by a chemical or electrochemical passivation layer (3) or oxidation layer (3).

Instead of 50 layers thus a technically producible solvation-sensitive sensory material (e.g. responds to humidity) can be manufactured by choosing an inert sol/gel base layer of e.g. 100 nm thickness, a binding layer out of aminopropylsilane for more stable anchorage of the chains and a solvatable, at least partially 3D-folded sandwich out of 2 negatively charged polymers and 2 positively charged polymers=4 polymer layers with sequential arrangement A-B-A-B (together with mirror and nanoparticle layer=8 layers!). Choosing the more complex configuration allows manufacturing sensory films in a roller coater without high vacuum technology and/ or in standardized chemical reactors without printing technologies like gravure printing or flexo printing, which show insufficient performance in the nanometer range. Thus the configuration according to the invention allows color-homogeneous, technically practicable manufacturing for the first time and for the first time also manufacturing on 3D-objects of deliberate form at market-compliant costs. The combination of sensory surfaces with selectively permeable materials such as e.g. Sympatex, polyesters, polyacrylates, polymers co-extruded with starch grains or co-extruded porous polypropylene allows applying the films separated from the packaged goods and make their color change visible also from outside through the intact packaging. The color-changeable sensory surfaces according to the invention can be provided with suitable cover layers to e.g. render them sensitive to bacterial enzymes and then show a direct correlation with bacterial growth.

The sensor with color-changeable sensory surface is particularly utilizable as sensor for intelligent packaging on consumer goods, especially for simple indication of humidity, indication of condensation water, indication that a temperature limit has been exceeded, indication of the temperature history (temp-time), for indication of complex chemical information, of the pH-value, of ion concentrations, for indication of food deterioration, indication of living germs.

Carrier materials for the sensors are often films or filmflakes consisting of metal or metalized glass, mica, PP, or PET, metalized molded parts or punched parts. To yield a stable coating it is often necessary to cover the film e.g. out of aluminum first with an undercoating and corrosion protection layer of preferably 1-300 nm particularly preferably 3-150 nm—this can be done chemically, electrochemically or via sol/gel. Also ultrathin lacquers are applicable as layer (3). Thereafter the already described multi-molecule layer sandwich out of a number of at least partially folded polymer chains is applied onto this inert base layer via ionic binding. If need be covalent binding can also be used to increase the stability of the multilayer sandwich film. The fact that the color-reactive films show a structural color effect and that this effect is changed by the analyte avoids the limiting factor of analytics, the diffusion of partially toxic chemical reagents—this is particularly critical for food products and thus prohibited. The films according to this invention can provide a new safe product for the food industry as they show chemically sensitive color effects without soluble chemicals.

Also color-changeable sensory freeze-thaw indicator film tags according to the configuration described in this invention are accessible in an easy way, which are capable of giving an optically cognizable hint, whether a frozen article such as frozen food has in the following been thawed briefly or (for a longer period of time). A combination of the films with a freeze/thaw-reactive cover layer as described in this invention, which upon thawing releases e.g. humidity, an acid or base in a composite film that is waterproof from the outside is visualized by the color change of the sensory film.

Especially the combination of color-changeable sensory films with thermal energy, light and chemical inkjet printing (chemically reactive inkjet inks) proves to be particularly advantageous—thus the films can be labeled selectively and in a forgery-proof way.

By chemical, photochemical or thermal change of subdomains (hot embossing, imprinting of a chemical crosslinker, . . . ) the display of symbols or text can be made possible i.e. the sensor—in the configuration according to the invention—can be used as intelligent display.

Color-changeable sensory films for monitoring organic solvents and organic chemical vapors can be realized using hydrophobic polymer nets. A hydrophobic multilayer polymer system allows converting the concentration of volatile organic solvents in the gas phase into a reversible optical signal. Should the color effect not be sufficient for identification, a number of different color-changeable sensory films can also form a color array and the identification of the component can be deduced from the pattern identification. In particular the secondary chemical change of the polymer sandwich by the binding of low-molecular analyte-specific molecules allow setting up big selective color sensor arrays. The methods described in WO 2009/029964 of polymerizing polymers directly onto the particle surface (e.g. chain elongation of acrylates on an anchoring molecule with silanfunction, which can bind directly to metal oxide surfaces) or with "living radicals" as precisely controllable polymerization technology (precise chain lengths with narrow molecular weight distribution) are not suited for films, as they proceed too slowly, require toxic catalysts and are in most cases not oxygen-tolerant.

Nanoparticles (reference sign 6) out of corrosion resistant metals or semiconductors (e.g. Au, Ag, Cu, Pd, Ni, Co, Si, C, . . . ) are applied from solution via ionic (7) or chemical bonding or deposited via in-situ reduction (according to the literature, e.g. silver with dimethylformamide or via polyol chemistry) directly onto the surface of a polymer from precursor states.

Color nanoparticle (reference sign 6) are accessible by a number of techniques and are bound from solution of gas phase. Anionic dyes bind e.g. to polyethyleneimine, mordant dyes bind via complex formation with chromium(III), iron (III) or aluminum salts, disperse dyes are practically already nanoparticles, ingrain or developed dyes couple chemo-reactively. Cationic dyes bind to carboxylated and sulfonated polymers, vat dyes precipitate due to atmospheric oxygen. Metalized dyes and reactive dyes with particulate deposition are applicable as nanoparticles or all dyes, which are provided with pigment properties by lacquering at sulfone, phosphate or carboxyl groups. Dyes of the "Acid" or "Sunset" lines are exemplary here. Important pigments for nanoparticles (reference sign 4) are also monoazo pigments, disazo pigments, anthanthrone pigments, anthrachinone pigments, anthrapyrimidine pigments, chinacridone pigments, chinophthalone pigments, diketopyrrolopyrrole pigments, flavanthrone pigments, indanthrone pigments, isoindoline pigments, isoindoline pigments, isoviolanthrone pigments, metalized pigments, perinone pigments, perylene pigments, phthalocyanine pigments, pyranthrone pigments, thioindigo pigments and triarylcarbonium pigments as well as oil-soluble and precipitable dyes of the groups: "Disperse", "Solvent" or "Sudan". Applicable inorganic nanoparticles (reference sign 4) are among others iron oxides, ultramarine, Berlin blue, carbon black, chromium oxide, manganese violet, metal sulfides, metal oxides and suboxides of copper, nickel, cobalt or palladium.

A typical configuration and sequence of the process is:

Layer A: metalized or metal-coated injection molded part, embossed part or film (surface clean and at least partially reflecting)

Layer B: distance layer for adjustment of the base color, sol/gel technique Duration approximately 15 minutes Layer C: covalent activation of adhesiveness by aminosilane within approximately 2-5 minutes (optional)

Layer D: binding of a negatively charged polymer layer by "bringing in contact" with a solution within approximately 2 minutes Layer E: binding of a positively charged polymer layer by "bringing in contact" with a solution within approximately 2 minutes Layer F: binding of a negatively charged polymer layer by "bringing in contact" with a solution within approximately 2 minutes Layer G: binding of a positively charged polymer layer by "bringing in contact" with a solution within approximately 2 minutes Layer H: binding of metal of dye nanoparticles from concentrated solution (>1%) within 1 minute In between the layers respective washing and drying steps for the prevention of mixing of coating media have to be introduced.

Layer I: Finally a "handling protection layer" is applied to exclude that particles detach from the sensor and reach the product—this is done by varnishing or lamination respectively with a suitable cover layer within approximately 2 minutes. Total duration of the process approximately 30 minutes. The process proceeds fully automated with an immersion bath robot (for 3D-parts) or an a roller coater (flat objects, films, . . . ). If the process is performed in a chemical reactor the reaction times must at least be multiplied tenfold (diffusion time, mixing time, longer washing times, more washing steps, . . . ) though a higher productivity is nonetheless granted due to the big reaction volume.

In the following a short description of the reference signs in the figures as well as illustrative explanations:

FIG. 1 shows a schematical illustration of the sensor with color-changeable sensory surface. The assignment of the reference signs should be done as follows:
1. sensory material
2. light wave reflecting surface
3. inert interlayer <300 nm
4. solvatable polymer molecule layer 1 (charged)
5. solvatable polymer molecule layer 2 (oppositely charged)
6. nanometric chromophore particles (up to 60 nm)
7. charged surface of the particles (6)

The + and − symbols indicate charged polymers or surfaces and point out their alternating build-up.

The assembly is in most cases covered with a polymeric embedding medium or varnish. Among others, analyte-permeable lacquers like e.g. acrylate lacquer with high humidity permeability, swelling gel polymers or hot glues and pressure-sensitive glues, which influence the chemical behavior of the pigments as insignificantly as possible can be used as binding agents.

Also porous polymer films on the basis of polyurethane, Sympatex or the like can serve as coating.

Figure 2:
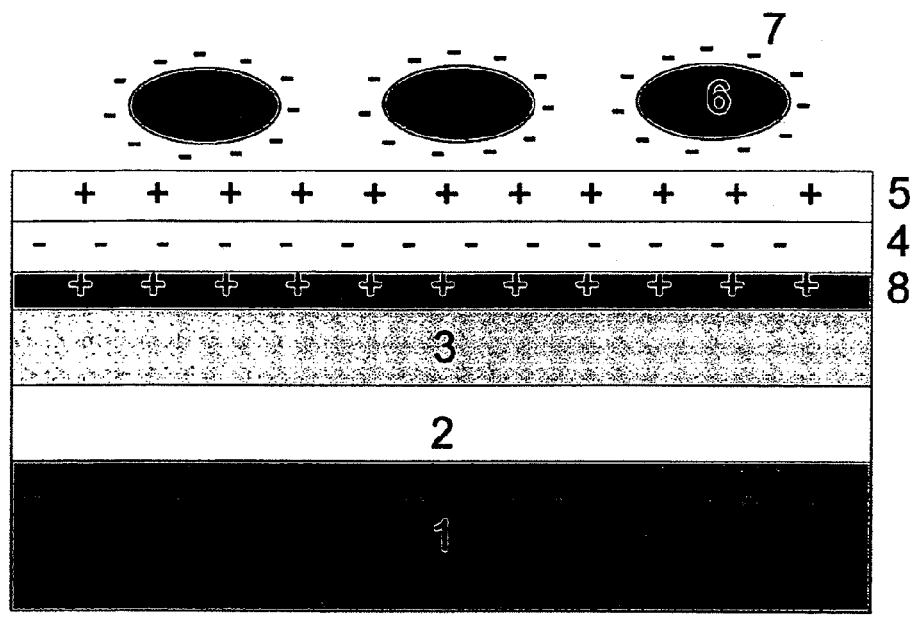

FIG. 2 shows a schematic illustration of the sensor with color-changeable sensory surface and adhesion-promoting agent. The assignment of the reference signs should be done as follows:
1. sensory material
2. light wave reflecting surface
3. inert interlayer <300 nm
4. solvatable polymer molecule layer 1 (charged)
5. solvatable polymer molecule layer 2 (oppositely charged)
6. nanometric chromophore particles (up to 60 nm)
7. charged surface of the particles (6)
8. adhesion-promoting agent with chemically reactive or ionically charged groups for binding of the first polymer molecule layer.

Figure 3:
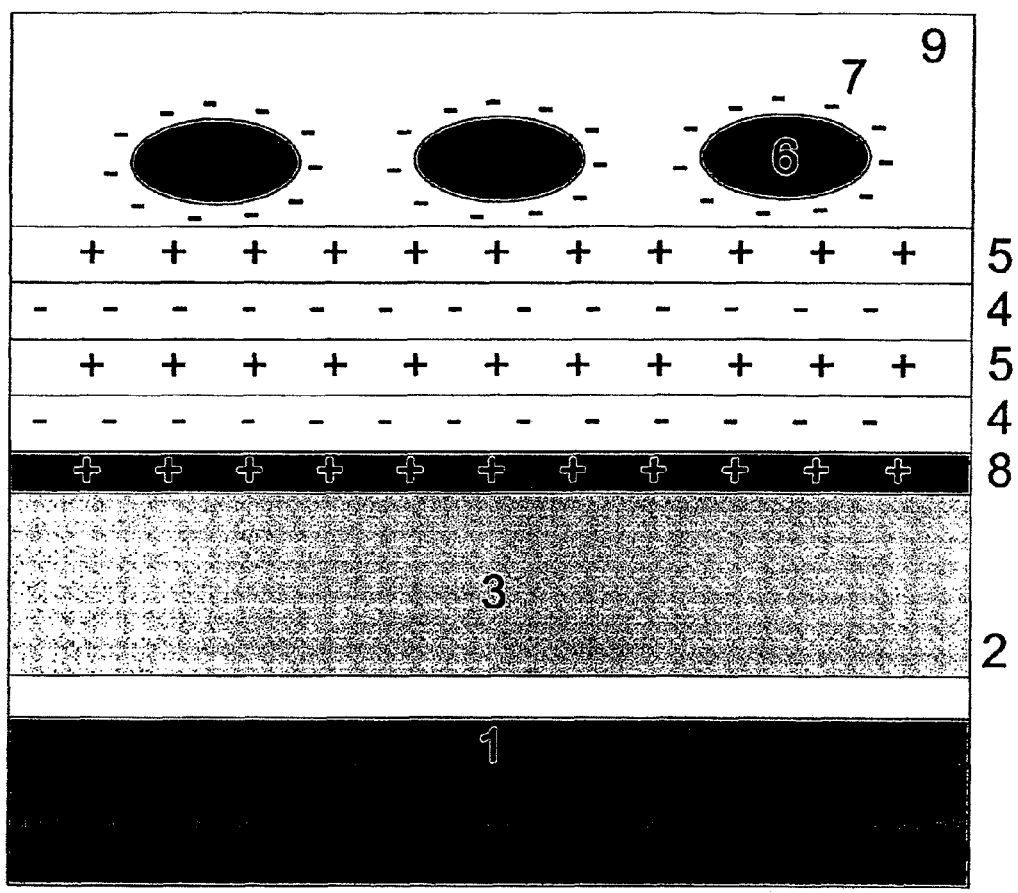

FIG. 3 shows a schematic illustration of the sensor with color-changeable sensory surface and boosted color effect. The assignment of the reference signs should be done as follows:
1. sensory material
2. light wave reflecting surface
3. inert interlayer <300 nm
4. solvatable polymer molecule layer 1 (charged)
5. solvatable polymer molecule layer 2 (oppositely charged)

The layers with reference signs 4 and 5 can be repeated in alternation at will. Often (2×2=) 4, 6, or 8 layers are used. The number of layers (even or uneven!) influences the behavior massively because in one case neutral and the in other case strongly charged layer sandwiches are generated. One (and only one!) of the polymers can be replaced completely or partially by charged nanoparticles,
6. nanometric chromophore particles (up to 60 nm)
7. charged surface of the particles (6)
8. adhesion-promoting agent with chemically reactive or ionically charged groups for binding of the first polymer molecule layer.
9. exterior matrix (top coat, binding agent, "handling protection layer".)

Figure 4:
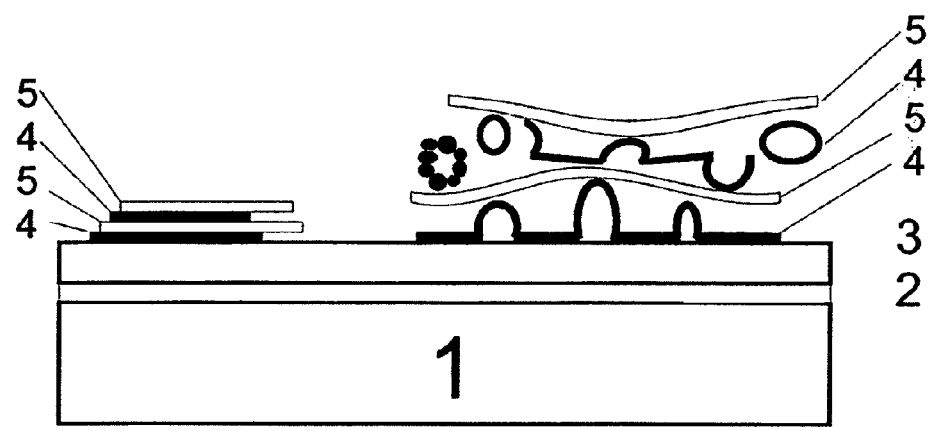

FIG. 4 shows a schematic illustration of the molecule structure of the layers according to the invention and of the molecule structure not according to the invention comparing the reference signs 4 and 5. The assignment of the reference signs should be done as follows:
1. sensory material
2. light wave reflecting surface
3. inert interlayer <300 nm
4. solvatable polymer molecule layer 1 (charged)
5. solvatable polymer molecule layer 2 (oppositely charged)

Left: molecule layers (4,5) directly bound upon each other completely without folding (normal conformation)—not according to the invention Right: molecule layers (4, 5) with at least partial folding of at least one chain—according to the invention; the chain allows penetration of solvent.

The invention is explained by examples of use:

Example 1

3D-Sensors & Films

An optional material is degreased and metalized by conventional techniques (wet-chemical, ABS technology, galvanic, vacuum, . . . )—gas phase metallization is appropriate for more noble metals than aluminum. The core can be out of plastics in favor of cost-efficiency but also out of ceramics, glass or full metal. Alternatively punched or embossed part, reflecting granulates or metal flakes are used.

Films are in most cases metalized with aluminum. Alternatively aluminum foils, stainless steel foils, nickel, chromium and titanium foils as well as copper and copper alloy foils, in the massive or laminated form or as coating can be used.

Example 2

Semitransparent Configuration

The configuration conforms to the exchange of the layers with reference signs 2 and 6.

First a semitransparent layer out of metal or dye is applied onto transparent objects with conventional techniques—this layer corresponds to the reference sign 6. It is coated with an inert layer (3) as usual.

After coating with the polymers (4+5) a nearly non-transparent, reflective layer (2) in most cases out of metal is applied instead of the usual layer 6. A dense layer out of reflective nano- or microparticles is well suited here. This configuration allows viewing the color from the backside.

Especially for packaging this configuration is advantageous, as the quality of the product can be evaluated from the outside without opening the packaging.

Beispiel 3

Application of the Inert Layer (3)

The inert layer is in most cases a sol/gel layer. Alternatively a number of most often electrochemical techniques can be used. Here typical raw materials are metallates of titanium (e.g. titaniumethoxylates), silanes like e.g. tetraethoxysilane, zirconium metallates or similar compounds, which react mostly with water by hydrolysis first to hydroxides and after thermal treatment to cross-linked, chemically mechanically stable oxides with good surface adhesiveness. A number of commercial products can be used for this purpose. The layer thickness of the mostly precipitated nanoparticulate layers is, depending on the application, up to 0.5 micrometers.

As exemplary solutions serve:
5 liters of alcohol
1.25 liters of water
300 ml of 25% ammonia
1 liters of tetraethylorthosilicate The solution should be freshly prepared and is not stable. The solution is either freshly added to the reactor basin or, in the case of film coating, actively mixed in a mixing chamber directly before the film and applied to the film (plunged, sprayed, coated by curtain coating, . . . ).

The layer thickness that can be yielded in one pass is approximately 100 nm in most cases—thicker layers are created by repeated coating.

Example 4

Adhesion-Promoting Agent for the First Polymer Layer

As many polymer layers are extremely structurally reactive (strong layer tension), they must be chemically bonded to the surface of the carrier material or of the inert cover layer (3) respectively. For this purpose mostly silanes are used.

The silane is in most cases sprayed onto the oxide layer or applied with other technologically common methods. The reaction occurs within a few minutes—the excess is removed. Most often mono-, di- or trimethoxy-, ethoxy- or chlorosilanes with suitable functional groups for binding of the polymer are used as silanes; in most cases glycidyl silanes or aminosilanes e.g. aminopropyl-triethoxysilanes are used. Glycidyl silanes react chemically covalently with the first monolayer of an aminic polymer e.g. with polyethyleneimine; aminosilanes bind polymers ionically with acidic groups:

As exemplary solutions serve:
1 liter of alcohol (not to long-chained or hydrophobic respectively)
15 ml 3-aminopropyl-triethoxysilane
Reaction time: 1-5 minutes
Without water the solution is stable.

Example 5

Application of the Multi-Molecule Layers of Films

After application of the aminic adhesion-promoting agent the films are guided through a bath containing a negatively charged polymer and this polymer is left on the film and then washed with water or a water-solvent mixture. Only one molecule layer binds at a time. Depending on the required layer thickness both steps can be repeated at will—per step the layer thickness increases by about 2-20 nm. Layer of 2 nm thickness are nearly unreactive—layers of more than 20 nm are in most cases not bound strongly enough and thus instable.

On a roller coater immersion and spraying modules are arranged in alternation with washing modules and the process is performed fully-automated.

As solutions serve:
1.) Positive Polymer
0.1 to 1% solution of polyethyleneimine, molecular weight 0.5 kD to megadalton in the solvent water containing up to 20% salt preferably e.g. sodium chloride or using a water-mixable organic solvent like alcohols, DMF, formamide, DMSO, NMP (the exact content depends on the product properties of the polymer and can cause massive changes in the molecular structure of the macromolecule even at deviations of +/−10%!). Lower polymer concentrations prolong the reaction time—too high concentrations are usually too viscous. Polymers with low molecular weight most often fold not sufficiently and bind weakly—too high molecular weight makes the layers highly viscous and the coating inhomogeneous.

2.) Negative Polymer
0.1 to 1% solution of acrylic acid or polymethylvinylether-copolymaleic acid, molecular weight 0.5 kD to megadalton, solvents and additives analogous to the positive polymer see above.

The thickness of the polymer molecule layers (4+5) are influenced by the selection of the deposition solution and its chaing folding and decreases with increasing charge of the chains of usually more than 3-8 nm per layer to approximately 2 nm per layer. Thereby the absorptive power of the solvent decreases dramatically, see FIG. 4. Too low charge of the chains leads to no binding and thus to no layer assembly. Acidic polymer solutions are thus preferably adjusted to pH=3.5, basic polymers arer buffered to approximately pH=7.5. To reduce of the ionic forces as desired, salts (often sodium chloride) are added to the solution. In the case of weak acids usually 0.1-0.25 molar, in the case of strong acids e.g. sulfonic acids around 1 molar.

If the ionic strength surpasses a critical limit the layer structure dissociates! Secondary chemical cross-linking of the layers is possible.

Example 6

Application of the Multi-Molecule Layers onto 3D-Objects

After application of the most often aminic adhesion-promoting agent, the metalized 3D-parts are put into a dipping basket or handled in a rotating basket system.

The basket is put into a bath containing a negatively charged polymer and left there for approximately 2 minutes, the polymer bath being stirred advantageously.

Then the basket is rinsed in water or in a water-solvent mixture.

Then the basket is put into a bath containing a positively charged polymer and left there for approximately 2 minutes, the polymer bath being stirred advantageously. Only one molecule layer of the respective polymer binds per dipping step. The dipping steps can be repeated at will depending on the required layer thickness. In the case of big objects (plates, . . . ), the objects are hung and moved from bath to bath—the respective infrastructure is available at all galvanization facilities.

The polymer solutions listed in example 5 serve as solutions.

Example 7

Polymers for Water-Sensitive Color-Changeable Sensory Films

Primarily all hydratable at least partially ionic macromolecules are suited for this purpose. According to the invention layers 4 and 5 consist of ionic polymers i.e. of polyacrylic acid, polymethacrylic acid, charged polymethacrylate, polysulfonic acids, polyethyleneimin, polyamines or their copolymers but also biological macromolecules are utilizable. Especially at least partially charged graft polymers and dendrimers yield highly reactive layers.

The exact reaction conditions of the coating influence substantially the subsequent structural behavior in analyte interactions e.g. in the case of water intercalation the water binding capacity of polymers. The selection of the deposition solution can influence the chain folding of the polymers. The thickness of the individual polymer monolayers decreases with increasing charge of the chains form usually 3 nm per layer to rounded 2 per layer. Thus the uptake of solvent is not or nearly not possible anymore and the sensors show no significant color change upon contact with water or (atmospheric) humidity.

Thus the coating is done from aqueous or aqueous organic solution and the charge of the polymers (4+5) is reduced by appropriately adjusting the pH-value and/or alternatively salt is added in order to reduce the effective ionic charge. In the case of acidic polymers (carboxylates, sulfonates, . . . ) the pH-value is usually increased to pH=3.5, for instance, in the case of basic polymers such as polyethyleneimines the pH-value is reduced to as far as pH=7. In the case of polymers with hydrophilic and hydrophobic domains the selective addition of organic solvents is necessary for optimal chain folding.

Example 8

Binding of Nanoparticles (6)

The carrier material (1+2+3) with the reactive polymer molecule monolayer sandwich (layers 4+5, usually deposited manifold) is coated with a suspension of very fine particles, preferably with a size of less than 60 nm, selected from the group of metals V, Cr, Mn, Co, Ni, Cu, Ag, Sn, Pb, C, Si, Ge, and Bi. The process proceeds via ionic attraction of the charged nanoparticles at the last oppositely charged polymer surface. The metallic nanoparticles are usually present as a suspension of preferably more than 1 mass percent and usually can be bound within less than one minute as a dense layer to the last polymer layer. To allow development of a strong color the mean mass thickness of the metallic particle layer should be around 5 nm, if using chromphoric particles more proportional to their extinction coefficient (mass-thickness). In case the layer exhibits an absorption-coefficient that is too low an additional dip-coating step in an oppositely charged polymer allows deposition of a second layer of nanoparticles (e.g. negative silver colloid+polyethyleneimine with low molecular weight+a second layer of negative silver colloid).

Example 9

Silver as Nanoparticle

Silver nanoparticles in highly concentrated solutions with some mass percent of silver are prepared by simple means. Silver nanoparticles in solution are commercially available and as e.g. conducting silver paste or antibacterial silver widely in use. The coating is done via ionic binding of the nanoparticles with a mostly negative charge at the last most outside-positioned positively charged polymer layer within seconds from aqueous or organic solution.

Example 10

Carbon as Nanoparticle

The activated carrier material with a strong ionic charged surface (4 or 5) (mostly positive) is mixed with a carbon black dispersion. By addition under binding conditions a carbon-containing insoluble layer is precipitated onto the substrate. The process proceeds by ionic attraction of mostly negatively charged carbon black particles at the last oppositely-charged surface layer. The carbon black particles usually 13-40 nm in size (and e.g. commercially available from Evonik®) are usually offered as a suspension of preferably more than 1 mass percent and can be bound from this solution within less than one minute to the last polymer layer. Often these sensory pigments exhibit a dark character and a lusterless gloss due to deposited aggregated carbon black agglomerates.

Example 11

Top Layer

The carrier substrates coated according to the procedures described in examples 1-9 are deposited preferably mixed with a polymer or the polymer is applied onto the films. The thickness of the covering top layer is in between 0.1 to 300 µm, preferably between 1 to 50 µm. The top layer is not just used to protect the material surface but moreover can possess chemically important permeation-selective properties as e.g. water vapor is allowed to pass with low resistance whereas ions are blocked effectively (can be achieved by non-ionic acrylate esters). The lacquers are usually coated by spray, doctor blade or dip coating techniques. If using lacquers, which swell intensely, it is necessary to account for the massive shear stress on the layers (and to reduce or compensate it)—otherwise the layer setup breaks apart.

Example 12

Platelet-Type Carrier Substrates (1)

It is moreover possible to replace metallic-silvery reflecting carrier substrates (1) by highly refractive colorful reflecting ones. These are e.g. Iriodin® 100, Silver Pearl, 10-60 µm; Iriodin® 103, Rutile Sterling Silver, 10-60 µm; Iriodin® 111, Rutile Fine Satin, 1-15 µm; Iriodin® 119, Polar White, 5-25 µm; Iriodin® 120, Lustre Satin, 5-25 µm; Iriodin® 123, Bright Lustre Satin, 5-25 µm; Iriodin® 153, Flash Pearl, 20-100 µm. These colorful-shining effect pigments (e.g. interference pigments of the 200 or 700 series) change their color depending on the viewing angle, the color changes and exhibits iridescence. In combination with coloring agents strong effects with an effective color change can be obtained. Well known are e.g. Iriodin® 211, Rutile Fine Red, 5-25 µm;

Iriodin® 221 Rutile Fine Blue, 5-25 μm; 23 Iriodin® 223, Rutile Fine Lilac, 5-25 μm or Iriodin® 231 Rutile Fine Green, 5-25 μm. Similar effects are observed with Iriodin® flash-interference pigments and Iriodin® ultra-interference pigments.

Using iron oxide-containing Iriodin® effect pigments of the 300 and 500 series, usually pigments with golden or metallic luster, a number of golden, bronze, copper, and red gloss effects can be realized.

All pigments cited above can be used directly or after a preceding coating on a base carrier as intelligent color-changing sensory materials allowing nearly all desired color-change variations. Especially intense warning colors (red, orange and yellow) as basic colors allow, due to the present invention, warning the customer in case of altered (deteriorated) products.

Example 13

Nanoparticles as Partial Polymer Replacement

One of the charged polymers can moreover be replaced by a charged nanoparticle—replacing both polymers (4 and 5) completely is not possible. Following the application of the mostly amine-based adhesion-promoting agents the films are guided through a bath with negatively charged polymer and left there for around 2 minutes, further on washed with water or a water-solvent mixture. Then the film is immediately dipped into a bath containing a positive polymer and left there for around 2 minutes, then washed with water or a water-solvent mixture. Following the coating with positive polymer, the films are exposed to a bath with silica nanoparticles around 7-40 nm in size and incubated for 2-10 minutes, further on washed with water or a water-solvent mixture. Subsequently the process is continued with positive polymer as usual.

As solutions polymers as described in example 3 can be used. As nanoparticles various types can be employed e.g. Ludox, carbon black, or nano-titanium dioxide—strongly scattering particles destroy the resonance color by imposing a strong scatter light.

Example 14

Proteins as Partial Polymer Replacement

In analogy to example 12 one of the charged polymers can be replaced by an identically charged biological polymer e.g. protein (similarly DNA, polysaccharides, . . . ). The simultaneous replacement of both ionic organic polymers (4+5) by folded biopolymers is only possible if a significantly reduced stability is accepted, due to the fact that both types of polymers are bound to each other only by an insufficient number of interaction sites. The limitation is not valid for DNA, RNA or pseudo-nucleic acids due to the fact that these molecules are only weakly folded and thus are able to interlock layer by layer. Thus, mostly a single or only a few layers are replaced by biological polymers—e.g. the topmost layer is implemented as a protein layer. A layered system made from DNA and polyamines exhibits good sensory properties and might be used as an analytic structure for nucleases. Layered systems made out of proteins can e.g. make use of their enzymatic properties.

Example 15

Organic Nanoparticles

As an alternative to the use of inorganic nanoparticles organic nanoparticles made from thermo-stable color pigments preferentially produced by sublimation, precipitation from solution or ultra-fine grinding can be used. Examples of these colored pigments are dyes employed in ink-jet technology e.g. phthalocyanine, chinacridone, perylene, perinone, thioindigo, anthraquinone, anthrapyrimidine, alavanthrone, pyranthrone, anthanthrone, dioxazine, triarylcarbonium, quinophthalone or diketopyrrolopyrrole pigments. Optimally the particles must possess adsorptive properties and are preferentially charged to be applied similarly to metallic particles by dip coating within seconds to a few minutes to the outer polymer layer as a dense nanofilm. Sulfonated phthalocyanine pigments are suited to bind to a strongly positively charged polymer and moreover exhibit a high light fastness.

Example 16

Sensor with Text and Symbol Output

Usually color-change based sensors or test stripes are supplied with a comparative scale to ease the application for the customer. The setup due to the present invention allows directly displaying text or symbols. As an example a sensor according to claim 1 with a layer sandwich out of humidity-reactive polymers (polyamines and a polycarboxylic acid) is locally cross-linked by thermal embossing at 250° C. for around 1 second. Amide bonds are formed in between the macro molecules—at the particular spot the material swells less upon contact with humidity and following contact with humidity e.g. the visible text-output "wet" appears. In a non-swollen state the text is not visible. This behavior allows the customer seeing a clear message without an instruction leaflet or a comparative scale.

Example 17

Alternative Technique for Text or Symbolic Output

Alternatively it is possible, in analogy to example 16, to achieve the effect by printing with a nonvolatile acid. The print is visible immediately by a different color—following contact with humidity (optimally adjusting the effect) the printout disappears. The text "too dry" would not be readable any more.

The invention claimed is:

1. Sensor with color-changeable sensory surface characterized in that alternately at least one molecular layer of a positive charged polymer via ionic forces is bound to a further layer of a negatively charged polymer and within these charged polymeric layers a solvent is embedded, by which these polymer layers swell at least 10%, and at the last charged polymer monolayer colored, preferably metallic or semiconducting, nanoparticles are bound and the sum of the thicknesses of the inert interlayer and all polymer layers is at least 40 nm but less than 500 nm, and the layered setup exhibits a changing interference by interacting with the analyte with a color that is visible to the human eye or measurable in the infrared, induced by an optical interference of the material surface and the layer of nanoparticles.

2. Sensor with color-changeable sensory surface according to claim 1 characterized in that at least 4 alternating positively and negatively charged polymer molecule monolayers are deposited.

3. Sensor with color-changeable sensory surface according to claim 1 characterized in that more than 5 charged polymer monolayers are deposited and the overall number of deposited layers including the particle layer is more than 7 and that the polymer chains take up more than 30% weight percent of solvent, relative to the weight of the polymer, after getting in contact with it.

4. Sensor with color-changeable sensory surface according to claim 1 characterized in that the basic color is adjusted by selection of the thickness of the inert layer.

5. Sensor with color-changeable sensory surface according to claim 1 characterized in that as charged polymers (4, 5) polyacrylic acids, polymethacrylic acids, polyvinylsulfonic acids, aromatic polysulfonic acids preferably polystyrenesulfonic acid, polyphosphonic acids, polycarboxylic acids preferably polymaleic acids or hyaluronic acid, charged cellulose derivatives, polyethyleneimine, polyamines preferably polyallylamine, poly(diallyldimethylammonium), polyimidazoles, polyamino acids, or biological polymers preferably proteins or nucleic acids or mixtures and copolymers thereof and or grafted polymers with non-charged polymers preferably acrylamides or polyethyleneglycoles are employed.

6. Sensor with color-changeable sensory surface according to claim 1 characterized in that the charged polymers have particulate structure.

7. Sensor with color-changeable sensory surface according to claim 1 characterized in that for transparent carrier materials the reflecting layer and the nanoparticles layer are exchanged to allow the visibility of the color response from the backside through the sensor material.

8. Sensor with color-changeable sensory surface according to claim 1 characterized in that the nanoparticles are charged and are bound to the oppositely charged last polymer layer and the charge is preferentially introduced by coating the particles with charged polymers, thiols, amines, carboxylates, charged phosphor-oxy-compounds and the coating with nanoparticles is done preferentially by spraying or dip-coating with a suspension.

9. Sensor with color-changeable sensory surface according to claim 1 characterized in that the charged nanoparticles are preferably out of silver, palladium, gold, platinum, rhodium, copper, indium, aluminum, nickel, cobalt, chromium, iron, vanadium, molybdenum, tungsten, titanium, niobium, tantalum, zirconium, tin, germanium, bismuth, antimony, carbon or silicon and their alloys and are deposited from a concentrated suspension of more than 0.1% metal, preferably more than 0.5% metal, more preferably 1% metal.

10. Sensor with color-changeable sensory surface according to claim 1 characterized in that the nanoparticles with a diameter in at least direction of their axis have a dimension of less than 40 nm and are preferentially selected from the group of anthraquinone pigments, carbon black pigments, quinacridone pigments, diketopyrrolopyrrole pigments, phthalocyanine pigments, azo or isoindoline pigments and or are anionic or cationic dyes, mordant dyes, dispersion dyes, developing or coupling dyes, vat dyes, metal complex dyes, reactive dyes with particulate depositions and or pigments formed by lacquering with sulfate, phosphate, carboxylate or amine groups.

11. Sensor with color-changeable sensory surface according to claim 1 characterized in that the polymers are deposited as molecular monolayers from solution depositing in each step only one molecular layer and the coating is performed by alternating bringing in contact, preferably by dipping or spraying, with the particular polymer.

12. Sensor with color-changeable sensory surface according to claim 1 characterized in that before the first polymer the surface is covalently activated preferentially using amino- or epoxysilanes.

13. Sensor with color-changeable sensory surface according to claim 2 characterized in that the inert layer on the reflecting sensor surface is out of silica or organo-silica (crosslinked organosilanes) or analogue titanium, aluminum or zirconium compounds and is deposited via a self-thickness-limiting process preferably via hydrolysis of organometallic precursors in a solvent.

14. Sensor with color-changeable sensory surface according to claim 1 characterized in that the inert layer is deposited via hydrolysis of organosilanes from an aqueous organic solvent and is preferentially negatively charged.

15. Manufacturing process for a sensor with color-changeable sensory surface according to claim 1 characterized in that the inert layer is deposited by immersion in or spraying of organosilanes in an aqueous organic solvent over the sensor within a reaction time of more than 2 minutes but less than two hours, preferably 5-30 minutes, at a temperature in between the freezing point and the boiling point of the solvent.

16. Manufacturing process for a sensor with color-changeable sensory surface according to claim 1 characterized in that the inert layer is applied by spraying, immersion, roller-coating, or curtain-coating from aqueous-organic solution onto the film preferentially by a roller-coater and the evaporation of the solution is retarded preferably using a reaction chamber of less than 1 cm height, more preferably less than 200 µm or by choosing a solvent with a higher evaporation point or by using a reactant saturated atmosphere.

17. Manufacturing process for a sensor with color-changeable sensory surface according to claim 1 characterized in that the inert layer is applied by dipping the plate, chips or carrier particles into an aqueous-organic solution of organosilanes preferably in a tank-reactor and the risk of explosion is avoided by choosing an alcohol with a high flame-point that is significantly higher than the chosen reaction temperature.

18. Manufacturing process for a sensor with color-changeable sensory surface according to claim 1 characterized in that the inert layer is provided with a positively charged top layer by reaction with aminosilanes.

19. Manufacturing process for a sensor with color-changeable sensory surface according to claim 1 characterized in that the thickness of the polymer molecule layers is influenced by choosing the proper deposition solution controlling the chain folding by controlling the charge of the polymers via adjusting the pH in a way to reduce their charge or by adding salt to reduce effective ion charge or by mixing the water with a suitable solvent.

20. Manufacturing process for a sensor with color-changeable sensory surface according to claim 1 characterized in that the polymers are partially titrated with counter ions to adjust the water binding capacity preferably sodium, potassium, lithium, magnesium, calcium, zinc, manganese or primary, secondary, tertiary or quaternary amines or their mixtures.

21. Sensor with color-changeable sensory surface according to claim 1 characterized in that the sensor is coated with a water-vapor permeable film blocking liquid water preferably selected from porous extended polypropylene or polyethylene, polyamides, cellulose and its derivates, polyurethane, or similar polymers with high water-vapor permeability and that the films are preferentially mounted using an adhesive with similar properties or a diffusion-open coating-film is directly coated.

22. Sensor with color-changeable sensory surface according to claim 1 characterized in that the sensor is coated with a water-vapor permeable polymer of at least 100 nm thickness, preferably 1 µm thickness preferably an acrylate or methacrylate avoiding the addition of highly hydrated or ionic polymers which would allow corrosive liquid water and ions to permeate.

23. Sensor with color-changeable sensory surface according to claim 22 characterized in that the acyrlate or methacrylate ester carries an aliphatic side chain of less than 9 carbon atoms length preferably pure or mixed methyl, ethyl, propyl, butyl or ethylhexyl.

24. Sensor with color-changeable sensory surface according to claim 1 characterized in that the charged polymers are at least partially an enzymatically or biorecognitively active biopolymer, preferably nucleases, esterases, amidases, glycosidases, antibodies or lectines.

25. Sensor with color-changeable sensory surface according to claim 1 characterized in that the interaction with the analyte changes the interference color irregularly preferably forming the shape of a text, graphics or symbols reacting sensorial to a stimulus.

26. Sensor with color-changeable sensory surface according to claim 25 characterized in that the chemical change of the polymer layers for displaying symbols, graphics and or text is done by thermal embossing or preferably by flexo, offset, gravure, book or screen printing with rakel, curtain coater, inkjet or laser.

27. Sensor with color-changeable sensory surface according to claim 25 characterized in that symbols, graphics or text supplements or replaces the color comparison tables and is preferred in explaining the sensor result to the user.

28. Sensor with color-changeable sensory surface according to claim 25 characterized in that generating of a color pattern is done via local crosslinking of positive and negative polymer layers or by local incorporation of molecules binding to the polymer layers.

* * * * *